United States Patent
Weiss et al.

(10) Patent No.: US 10,849,587 B2
(45) Date of Patent: Dec. 1, 2020

(54) SOURCE OF ABDOMINAL PAIN IDENTIFICATION IN MEDICAL IMAGING

(71) Applicant: Siemens Healthcare GmbH, Erlangen (DE)

(72) Inventors: Alexander Weiss, Plainsboro, NJ (US); Atilla Peter Kiraly, Plainsboro, NJ (US); David Liu, Richardson, TX (US); Bogdan Georgescu, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 598 days.

(21) Appl. No.: 15/461,563

(22) Filed: Mar. 17, 2017

(65) Prior Publication Data
US 2018/0263585 A1   Sep. 20, 2018

(51) Int. Cl.
*A61B 6/00* (2006.01)
*A61B 6/03* (2006.01)
*G16H 30/40* (2018.01)
*G06T 7/00* (2017.01)
*G06K 9/62* (2006.01)
(Continued)

(52) U.S. Cl.
CPC .......... *A61B 6/5217* (2013.01); *A61B 5/4824* (2013.01); *A61B 5/7267* (2013.01); *A61B 6/032* (2013.01); *A61B 6/461* (2013.01); *A61B 6/50* (2013.01); *G06K 9/628* (2013.01); *G06K 9/6256* (2013.01); *G06K 9/6262* (2013.01); *G06T 7/0012* (2013.01); *G16H 30/40* (2018.01); *G16H 50/20* (2018.01); *G06K 9/46* (2013.01); *G06T 2200/24* (2013.01); *G06T 2207/10081* (2013.01); *G06T 2207/20076* (2013.01); *G06T 2207/20081* (2013.01); *G06T 2207/20084* (2013.01); *G06T 2207/30092* (2013.01); *G06T 2207/30096* (2013.01)

(58) Field of Classification Search
CPC ....... A61B 6/5217; A61B 6/032; A61B 6/461; A61B 6/50; A61B 5/4824; A61B 5/7267; G16H 50/20; G16H 30/40; G06K 9/6256; G06K 9/6262; G06K 9/628; G06T 7/0012
See application file for complete search history.

(56) References Cited

U.S. PATENT DOCUMENTS

2009/0226040 A1   3/2009   Zhou et al.
2009/0116737 A1   5/2009   Kiraly et al.
(Continued)

OTHER PUBLICATIONS

Deleger, "Developing and evaluating an automated appendicitis risk stratification algorithm for pediatric patients in the emergency department", J Am Med Inform Assoc 2013;20:e212-e220 (Year: 2013).*

(Continued)

*Primary Examiner* — Joanne M Hoffman

(57) ABSTRACT

To assist a physician in diagnosis of trauma involving abdominal pain, scan data representing the patient is partitioned by organ and/or region. Separate machine-learnt classifiers are provided for each organ and/or region. The classifiers are trained to indicate a likelihood of cause of the pain. By outputting results from the collection of organ and/or regions specific classifiers, the likeliest causes and associated organs and/or regions may be used by the physician to speed, confirm, or guide diagnosis of the source of abdominal pain.

11 Claims, 3 Drawing Sheets

(51) Int. Cl.
    *G16H 50/20*    (2018.01)
    *A61B 5/00*     (2006.01)
    *G06K 9/46*     (2006.01)

(56) References Cited

U.S. PATENT DOCUMENTS

| | | |
|---|---|---|
| 2010/0080434 A1 | 4/2010 | Seifert et al. |
| 2010/0094122 A1 | 4/2010 | Kiraly |
| 2012/0070055 A1 | 3/2012 | Liu et al. |
| 2013/0064439 A1 | 3/2013 | Khurd et al. |
| 2013/0282005 A1 | 10/2013 | Koch et al. |
| 2014/0012558 A1 | 1/2014 | Mansi et al. |
| 2014/0093153 A1 | 4/2014 | Sofka et al. |
| 2015/0031992 A1 | 1/2015 | Monga et al. |
| 2015/0177354 A1 | 6/2015 | Bachschmidt et al. |
| 2016/0350919 A1 | 12/2016 | Steigauf et al. |

OTHER PUBLICATIONS

Sethi, "Computer aided diagnosis system for abdomen diseases in computed tomography images", Biocybernetics and Biomedical Engineering, vol. 36, Issue 1, 2016, pp. 42-55 (Year: 2016).*

Lee, "Identifying Multiple Abdominal Organs From CT Image Series Using a Multimodule Contextual Neural Network and Spatial Fuzzy Rules", IEEE Transactions on Information Technology in Biomedicine, vol. 7, No. 3, Sep. 2003 (Year: 2003).*

Partial European Search Report dated Jul. 24, 2018 in corresponding European Patent Application No. 18161186.4.

Gaurav Sethi et al: "Computer aided diagnosis system for abdomen diseases in computed tomography images", Biocybernetics and Biomedical Engineering, vo 1 . 36, No. 1, Oct. 31, 2015 (Oct. 31, 2015), pp. 42-55.

\* cited by examiner ns. Further aspects and advantages of the invention are discussed below in conjunction with the preferred embodiments and may be later claimed independently or in combination.

SOURCE OF ABDOMINAL PAIN IDENTIFICATION IN MEDICAL IMAGING

BACKGROUND

The present embodiments relate to identifying a source of abdominal pain from medical imaging. In certain cases of trauma, patient care involves diagnosing the cause of abdominal pain via a computed tomography (CT) scan. Many patients leave the hospital without having the cause identified even with a CT scan. The lack of domain knowledge of the emergency department physicians and/or time limitations may result in miss-diagnosis or no diagnosis. Diagnosis for abdominal pain at the time of an emergency room visit depends on the doctor's discretion, experience, and time to examine the patient. Hence, the quality of care may vary.

SUMMARY

By way of introduction, the preferred embodiments described below include methods, systems, instructions, and non-transitory computer readable media for identifying a source of abdominal pain. To assist a physician in diagnosis of trauma involving abdominal pain, scan data representing the patient is partitioned by organ and/or region. Separate machine-learnt classifiers are provided for each organ and/or region. The classifiers are trained to indicate a likelihood of cause of the pain. By outputting results from the collection of organ and/or regions specific classifiers, the likeliest causes and associated organs and/or regions may be used by the physician to speed, confirm, or guide diagnosis.

In a first aspect, a method is provided for identifying a source of abdominal pain. A patient is scanned with a computed tomography scanner. The scanning provides data representing an abdomen of the patient. The data is parsed into first and second portions representing first and second organs. One or more first deep-learnt machine-trained classifiers are applied to the first portion of the data with the application resulting in first likelihoods of multiple causes of abdominal pain for the first organ. One or more second deep-learnt machine-trained classifiers are applied to the second portion of the data with the application resulting in second likelihoods of multiple causes of abdominal pain for the second organ. An image of the patient is generated from the data. The image includes a plurality of the first and second likelihoods and the respective causes.

In a second aspect, a system is provided for identifying a source of abdominal pain. An image processor configured to detect multiple organs from results of the scanning by a medical scanner for scanning the patient. For each of the multiple organs, a machine-learnt classifier is configured to detect causes of the abdominal pain for the respective organ. A graphic user interface is configured to display the detected causes.

In a third aspect, a method is provided for identifying a source of abdominal pain. A medical image representing an abdomen of a patient is obtained. An image processor identifies separate organs, abdominal regions, or organs and abdominal regions in the medical image. Machine-learnt detectors separately determine a chance of each of a plurality of diagnoses for each of the organs, abdominal regions, or organs and abdominal regions. The chances and respective diagnoses for the organs, abdominal regions, or organs and abdominal regions are transmitted.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 4:
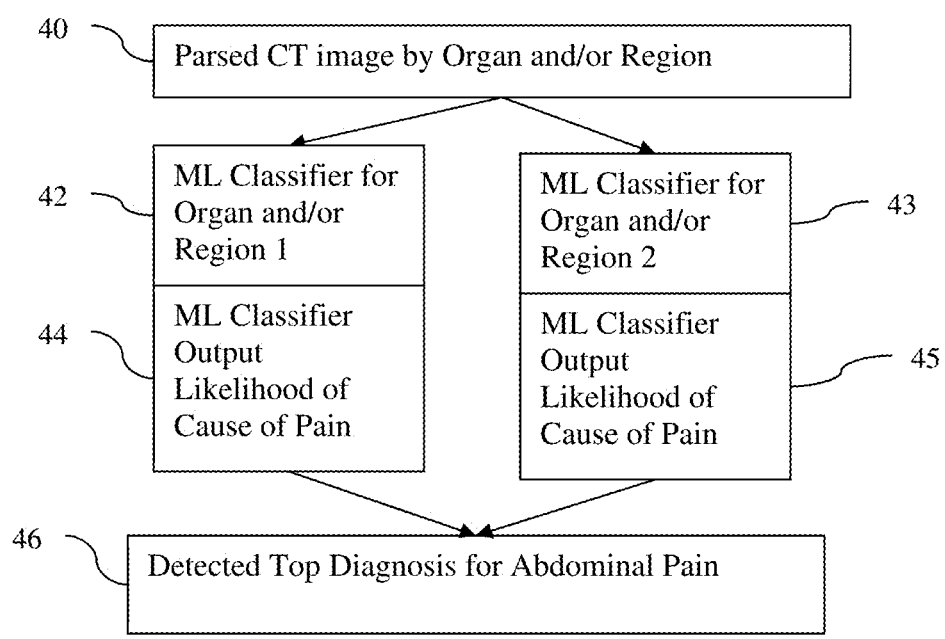
FIG. 4 illustrates classifiers being used.

Abdominal pain is automatically diagnosed using CT or other medical imaging. CT images are frequently acquired during emergency room visits for patients with abdominal pain. The CT image or images are parsed with the goal of determining the cause of abdominal pain based on the latest guidelines for different organs, regions, and/or causes. As shown in FIG. 4, guidelines or results from following the guidelines are incorporated into organ or region specific machine-learnt classifiers 42, 43. The machine-learnt classifiers 42, 43 are applied by a processor to the parsed CT image 40, resulting in rapid, full analysis of the organs or regions to assist in diagnosis. The top diagnosis 46 or most likely diagnoses for abdominal pain are detected and presented to the physician. After performing the image parsing and detection by organ or region, the results are presented in a user interface.

The automated system rapidly assists physicians in examining abdominal CT images with an emphasis on finding or suggesting the cause of the pain 44, 45. Since the process is automated, the full analysis of the data may be performed even when the physician is under a great work load. This diagnosis assistance for abdominal pain may be used during an emergency room visit and/or prior to trauma surgery.

Figure 1:
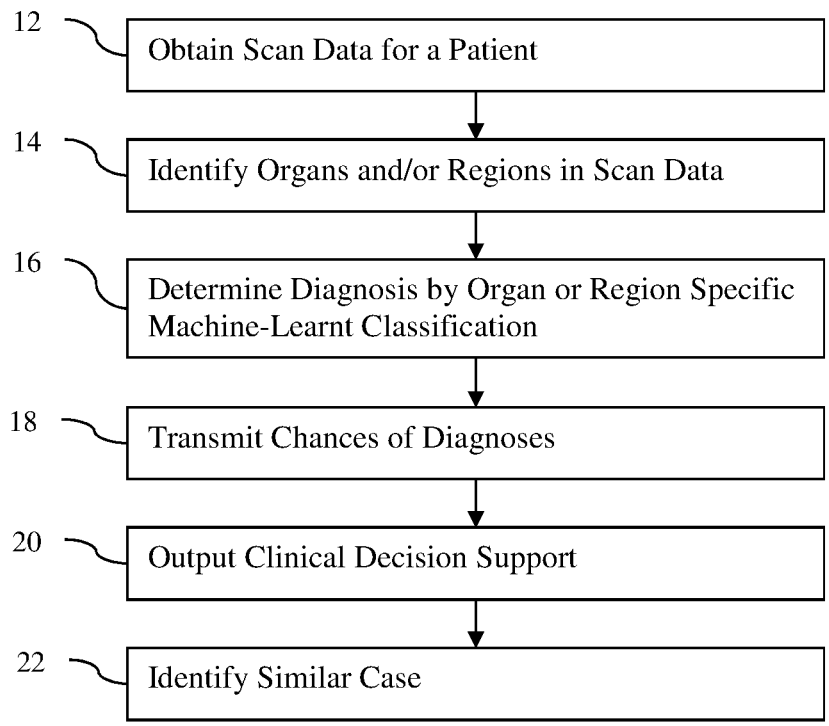
FIG. 1 is a flow chart diagram of one embodiment of a method for identifying a source of abdominal pain.

FIG. 1 shows one embodiment of a flow chart of a method for identifying a source of abdominal pain. The abdomen includes various organs and/or regions. It may be difficult to assign abdominal pain to a specific organ or region, let alone a specific cause. By parsing scan data and applying organ or region specific machine-learnt classifiers, the likeliest causes of the abdominal pain for a specific patient are identified. The collection of classifiers operating together may comprehensively assist a physician with diagnosis of abdominal pain.

The acts are performed in the order shown (e.g., top to bottom) or other orders. For example, acts 18, 20, and 22 are performed in any order.

Additional, different, or fewer acts may be provided. For example, the method is performed without one, two, or all of acts 18, 20, and/or 22. As another example, acts for configuring a medical scanner and/or therapy are provided.

Figure 3:
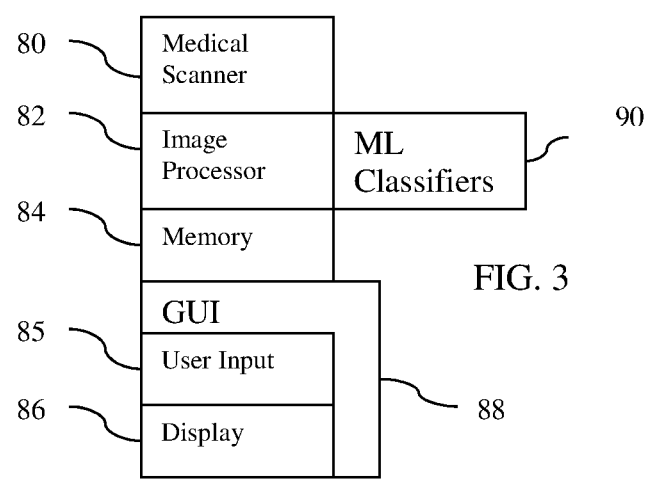
FIG. 3 is one embodiment of a system for identifying a source of abdominal pain.

The acts are performed by the system of FIG. 3 or another system. For example, act 12 is performed by a processor accessing a memory, transfer over a network, and/or by scanning by a medical scanner. Acts 14, 16, 18, and/or 22 are performed by a computer, processor, the medical scanner, a remote server, or a workstation. These four acts are performed by the same or different devices. Act 20 is performed by a graphic user interface or display.

In act 12, one or more medical images or datasets are acquired. The medical image is a frame of data representing the patient. The data may be in any format. While the terms "image" and "imaging" are used, the image or imaging data may be in a format prior to actual display of the image. For example, the medical image may be a plurality of scalar values representing different locations in a Cartesian or polar coordinate format different than a display format. As another example, the medical image may be a plurality red, green, blue (e.g., RGB) values output to a display for generating the image in the display format. The medical image may not yet be a displayed image, may be a currently displayed image, or may be previously displayed image in the display or other format. The image or imaging is a dataset that may be used for anatomical imaging, such as scan data representing spatial distribution of anatomy of the patient.

The medical image or scan data is obtained by loading from memory and/or transfer via a computer network. For example, previously acquired scan data is accessed from a memory or database. As another example, scan data is transmitted over a network after acquisition from scanning a patient. In other embodiments, the medical image or scan data is obtained by scanning the patient.

The scan data is obtained from scanning as a part of an emergency room visit by the patient. In response to trauma, a medical scan is performed to assist in diagnosis of a source of abdominal pain. The scan data is acquired by scanning at that time. The obtained scan data is from the scanning or by accessing previously acquired scan data. In alternative embodiments, the scan data is obtained by scanning during an appointment or routine examination outside the emergency context.

Any type of medical image may be used. In one embodiment, CT scan data representing a patient is acquired. CT scan data is acquired by rotating a source of x-rays and an opposing detector about a patient. Any range and/or path of travel may be used, such as rotating along a helical path of travel. C-arm or other x-ray imaging may be used instead. Based on the received detected intensities, a three-dimensional representation of the patient (i.e., the density or absorption as a function of voxel or location) is generated by computed tomography processing. Alternatively, the scan data represents a two-dimensional cross-section of the patient. In other embodiments, other types of scan data or medical image are obtained, such as magnetic resonance, x-ray, ultrasound, positron emission tomography, single photon emission computed tomography, or other medical imaging modality.

Data representing an interior region of a patient is obtained. The frame of data represents a one, two, or three-dimensional region of the patient. For example, the frame of data represents an area (e.g., slice) or volume of the patient. Values are provided for each of multiple locations distributed in two or three dimensions.

The data represents an abdominal region of the patient. The scan data may include the upper torso, legs, or other parts as well. The scanning is over at least part of the abdomen of the patient. More than one region and/or organs are represented by the scan data. For example, the stomach, liver, kidney, gallbladder, appendix, pancreas, spleen, uterus, lower intestine, and/or upper intestine are represented. Regions of the abdomen may be represented, such as lower, upper, digestive, or blood processing or filtering regions. The regions may include one or more organs, no organs, and/or parts of organs.

In act 14, an image processor identifies separate organs, abdominal regions, or organs and abdominal regions in the medical image or scan data. Specific organs and/or regions are identified. All or a sub-set of the organs and/or regions are identified by image processing. The user or a default may determine which organs and/or regions are identified. User input may be used to aid identification, such as in a semi-automatic approach. Alternatively, the image processor performs identification without user input of any location for an organ or region.

The identification parses one organ or region from another. The locations belonging to one organ or region are flagged differently than locations belonging to another organ or region. The specific organs or regions are found, parsing them from each other. Segmentation may or may not also be performed, such as extracting data for a given organ or region from the scan data. The identifying parses the scan data into portions representing different organs and/or regions. The partitioning is by a flag (e.g., detection and/or identification) or creation of separate datasets (e.g., segmentation).

Any now known or later developed identification may be used. For example, template matching, landmark detection, thresholding, filtering, or other image processing is applied to distinguish one organ or region from another. Image analytics software algorithms are run to parse the abdominal image into multiple organs and/or regions.

In one embodiment, the identification is performed with one or more machine-learnt classifiers. Machine learning uses training data of labeled or ground truth scan data to learn to distinguish one organ from other organs, one region from other regions, between organs, or between regions. The training data is used to train the classifier to parse or identify. One classifier may be trained to identify different organs and/or regions, or different classifiers may be trained to identify different organs and/or regions. A cascade or hierarchy of classifiers may be trained and used.

For machine training and application of a machine-learnt classifier, values for any number of features are extracted from the scan data. The values for textures of the tissues represented in the scan data are extracted. The texture of the tissue is represented by the measures of the scan data. The extraction of the values for each feature is performed for the abdominal tissues, avoiding application to other tissues outside the abdomen. Alternatively, the values for other regions outside the region of interest are extracted.

Each feature defines a kernel for convolution with the data. The results of the convolution are a value of the feature. By placing the kernel at different locations, values for that feature at different locations are provided. Given one feature, the values of that feature at different locations are calculated. Features for other texture information than convolution may be used, such as identifying a maximum or minimum. Other features than texture information may be used.

In one embodiment, the features are manually designed. The feature or features to be used are pre-determined based on a programmer's experience or testing. Example features include scaled invariant feature transformation, histogram of oriented gradients, local binary pattern, gray-level co-occurrence matrix, Haar wavelets, steerable, or combinations thereof. Feature extraction computes features from the medical image to better capture information distinguishing one or more organs or regions.

In another embodiment, deep-learnt features are used. The values are extracted from the scan data for features learned from machine learning. Deep machine learning learns features represented in training data as well as training the classifier, rather than just training the classifier from the manually designated features. The relevant features are automatically determined as part of training. This ability allows for the generic training on arbitrary data (i.e., training data with known outcomes) that may internally determine features, such as textures. By training the network with labeled outcomes, the network learns what features are relevant or may be ignored for parsing.

Any deep learning approach or architecture may be used. For example, a convolutional neural network is used. The network may include convolutional, sub-sampling (e.g., max pooling), fully connected layers, and/or other types of layers. By using convolution, the number of possible features to be tested is limited. The fully connected layers operate to fully connect the features as limited by the convolution layer after maximum pooling. Other features may be added to the fully connected layers, such as non-imaging or clinical information. Any combination of layers may be provided. In one embodiment, a series of convolutional and max pooling layers followed by two fully connected layers with additional coded input describing the past history input at the first fully connected layer is used. Additional, different, or fewer layers may be provided. In one alternative, a fully connected network is used instead of a convolution network.

The machine-learnt classifier, with or without deep learning, is trained to associate the categorical labels (output) to the extracted values of one or more features. The machine-learning of the classifier uses training data with ground truth, such as values for features extracted from frames of data for patients with known organs and/or regions, to learn to classify based on the input feature vector. The resulting machine-learnt classifier is a matrix for inputs, weighting, and combination to output a classification. Using the matrix or matrices, the processor inputs the extracted values for features and outputs the classification.

Any machine learning or training may be used. A probabilistic boosting tree, support vector machine, neural network, sparse auto-encoding classifier, Bayesian network, or other now known or later developed machine learning may be used. Any semi-supervised, supervised, or unsupervised learning may be used. Hierarchal or other approaches may be used. In one embodiment, the classification is by a machine-learnt classifier learnt with the deep learning. As part of identifying features that distinguish between different outcomes, the classifier is also machine learnt.

Additional information than scan data may be used for extracting and/or classifying. For example, values of clinical measurements for the patient are used. The classifier is trained to classify based on the extracted values for the features in the scan data as well as the additional measurements. Genetic data, blood-based diagnostics, family history, sex, weight, and/or other information are input as a feature for classification.

The machine-learnt classifier or classifiers identify the organs and/or regions represented in the scan data. The classifier classifies the organ or region of the patient from the extracted values of the features. The values are input to the machine-learnt classifier implemented by the image processor. By applying the classifier, the organ, region, organs, or regions are classified. This parsing of the scan data or medical image allows for application of organ or region specific prediction of one or more causes being a source of the abdominal pain. The classification (e.g., group of locations A are the liver and group of locations B are the kidney) parses or identifies.

In act 16, machine-learnt detectors determine a chance of each of a plurality of diagnoses for each of the organs and/or regions. After the parsing from the identification of act 14, the data specific to a particular organ or region is classified with a machine-trained classifier specific to that particular organ or region. For example, two organs are identified. One machine-learnt classifier is applied to the scan data identified for one of the organs, and another machine-learnt classifier is applied to the scan data identified for the other of the organs. Data identified differently than a given portion may be used with the data for that portion, such as including border information.

For a given organ or region, more than one machine-learnt classifier may be used. One machine-learnt classifier may be used for each possible cause of pain relevant for that particular organ or region. For example, multiple causes of pain for a given organ may include a tumor, lesion, inflammation, or bleeding. For the kidney, a kidney stone is another possible source of pain. Other organs may have other sources. A separate machine-learnt classifier is provided for each cause. One machine-learnt detector determines the chance for each diagnosis for the given organ or region. In other embodiments, a cascade or hierarchy of machine-learnt classifiers are applied for distinguishing between causes for a given organ or region. In alternative embodiments, a single machine-learnt classifier may output the chances for two or more causes of pain. The classifier determines the chances for any number of causes, such as outputting a chance for each of the possible causes for the given organ.

Any process may be used with the application of the machine-learnt classifiers. For example, further landmark detection and/or segmentation within the organ is provided. The scan data may be processed, such as filtered. Measurements may be made, such as an area or volume of a tumor or lesion. This further information may be used as part of an input feature vector, for calculating values of features, or for decision support provided in addition to any detection of the chance of being the cause of abdominal pain.

The same or different features are used by different classifiers to output the same or different information. For example, a classifier is trained for detecting a tumor, and another classifier is trained to detect bleeding. Both classifiers use different input feature vectors, but the same feature vectors may be used.

The machine-learnt classifiers are of the same or different types for the different organs or regions and/or the different causes. The training data is specific to a given organ or region and/or cause, so a same type of a machine-learnt classifier may result in different trained classifiers due to the difference in training data. Different types of machine training may be appropriate for different organs or regions and/or causes. Any of the machine training and corresponding classifiers discussed above for parsing may be used for determining the diagnosis of the source of pain.

In one example, a deep-learnt machine-learnt detector is used. The deep learning determines the features to be convoluted with the organ or region specific portion of the scan data and the classification output. For each organ or region, a custom deep learning or other machine-learnt software algorithm that has been trained to detect the most prominent clinical causes of abdominal pain parses the image portion for the organ or region and assigns likelihood scores for causes for each organ or region.

The training may be based on clinical studies, such as published and verified studies of a cause of abdominal pain. The study data and/or results may be used to train the classifier. As new studies are available, new classifiers or updated classifiers may be trained. Alternatively or additionally, training data and ground truth are acquired from a given institution, sharing across institutions, or on a regional basis.

The machine-learnt classifier outputs a chance of a cause of pain or chances of causes of pain. Based on the input scan data and/or values for the feature vector, the machine-learnt classifier is applied to the relevant portion of the scan data for a patient. The output is a likelihood of the cause being the source of abdominal pain. The classifier outputs a score, ranking, or percentage reflecting the chance of the cause being the source of pain. The likelihoods of each cause of multiple causes are determined. The likelihoods of the causes for each of multiple organs and/or regions are determined.

Figure 2:
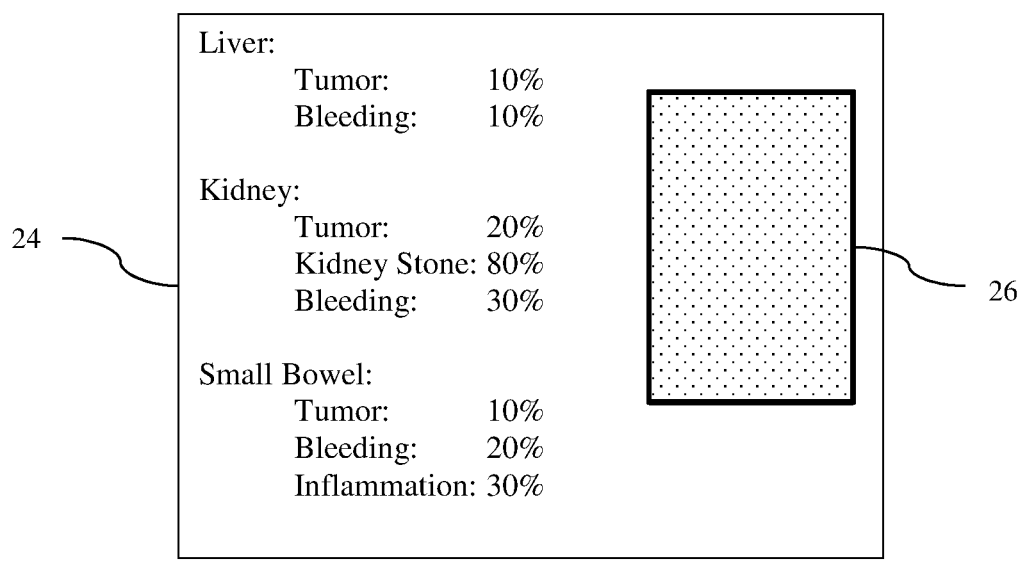
FIG. 2 illustrates an example graphic user interface (GUI) with results for various sources of abdominal pain as determined by respective machine-learnt classifiers.

FIG. 2 shows one example where the organs are the liver, kidney, and small bowel. One or more machine-learnt classifiers for each organ output the chance of each cause relevant to that organ being the source of pain. In this example, all the chances are 30% or less except for a kidney stone that has a chance of 80%. More than one cause may occur at a given time, so bleeding in the kidney and/or inflammation in the small bowel may be contributing causes of the pain. Other causes may contribute. The chance indicates the likelihood for guiding the physician in diagnosis.

The same or different machine-learnt classifiers may be trained to output other information. Prognosis, therapy response, effective treatment, or other information may be output.

In act 18, the image processor uses a memory interface, computer network interface, or display memory to transmit the chances and respective diagnoses for the organs, abdominal regions, or organs and abdominal regions. The transmission is to a display, such as a monitor, workstation, printer, handheld, or computer. Alternatively or additionally, the transmission is to a memory, such as a database of patient records, or to a network, such as a computer network.

Any of the chances or other guiding information to identify the source of the abdominal pain is transmitted. The identification of the organs and/or regions may be transmitted, such as providing separate anatomical images for separate organs or one image with the different organs highlighted differently. Alternatively, information derived from the output of the classification is transmitted, such as a most likely combination of multiple sources calculated from the chances for each individual cause by organ.

The chances are output as text or graphic information on an image. An image of the organ, abdomen, or location of interest within an organ or region is annotated or labeled with alphanumeric text to indicate the chance. In other embodiments, an image of the abdomen, organ, or region is displayed, and the chance is communicated as a symbol, coloring, graphic, highlighting or other information added onto the image. Alternatively, the classification is output in a report without the image of the abdomen.

FIG. 2 shows an example graphic user interface 24 presented as an image to the physician. The image indicates different organs and a list of the chances for each organ. An anatomical image 26 of a selected organ, of a region of interest for a selected cause, and/or of the abdomen is also provided. Other arrangements of information may be used in the image. Other information may be output as well. Other information includes values for the features, clinical measures, values from image processing, treatment regime, or other information (e.g., lab results).

All the predicted likelihoods of a given source of the pain may be transmitted for viewing by the physician. Alternatively, only a limited number of the likelihoods are provided. For example, the most likely source of pain is output. As another example, the N most likely sources of pain are output where N is an integer. Where N=3 in the example of FIG. 2, then the kidney stone, bleeding of the kidney, and inflammation of the small bowel and corresponding chances are output. Causes with lower chances (e.g., 20% or below) are not included. The number of chances transmitted may be below N, such as where a threshold amount is required (e.g., only 50% or greater so that N=3 only outputs the kidney stone chance of 80%).

Any resolution of the chances may be provided. While the classifier may provide integer resolution, the physician may be presented with the causes in multi-integer ranges (e.g., 10% or 25% ranges). The estimated chance may be rounded to the nearest or lower end of the ranges. For example, the chances are presented in 25% increments (e.g., 0%, 25%, 50%, 75%, 100%). Given an approximate abnormality detection with percentage confidence (e.g., 0, 25, 50, 75, or 100%), the top N items may be selected and shown to the physician along with the likelihood. Binning the chances into ranges may avoid an appearance of precision in the prediction, encouraging the physician to more thorough review.

The physician may select each cause or organ on the image. In response to the selection, the image 26 is altered to show the scan data rendered for the region of interest associated with the cause or the organ associated with the cause. The selection may also provide a more specific estimate, such as 54% instead of the approximate or rounded 50%. By transmitting the image during an emergency room visit or other trauma situation, a physician may be provided with clues or information to assist in diagnosing the source of the abdominal pain.

In act 20, the image processor or other processor outputs clinical decision support with the image. Decision support information, such as treatments, risks, guidelines, or other information, are output. Diagnostic rules for verifying the cause, such as based on guidelines or studies, may be output as decision support.

The physician may select the diagnosis believed to be accurate. Decision support is provided for the selected cause. Alternatively, decision support is provided for any selected cause to assist in determining the actual cause for the patient.

In act 22, the image processor or other processor identifies one or more similar cases to assist in diagnosis or treatment planning. A database includes chances, anatomical images, measurements, and/or other information for other patients treated for abdominal pain. Their outcomes may or may not be known.

The likelihoods in combination, such as the N likelihoods, are matched to the patients of the database. Other patients with a similar combination of likelihoods are identified. Other information in addition to or instead of likelihoods may be used to match. Any measure of similarity may be used. More than one other case may be matched, such as presenting a list or a statistical analysis based on the matching.

The previous matching case or cases are retrieved from the database for review by the physician. Previous cases with the same or similar diagnosis may be retrieved for the physician to compare diagnosis and treatments.

FIG. 3 shows a system for identifying a source of abdominal pain. The system implements the method of FIG. 1 or another method to output detected causes of abdominal pain, such as shown in FIG. 2. Results of scanning a patient are used to detect various possible causes of abdominal pain, helping a physician narrow down the options for diagnosis.

The system includes a medical scanner 80, an image processor 82, a memory 84, a graphical user interface (GUI) 88 with a user input 85 and a display 86, and machine-learnt classifiers 90. Additional, different, or fewer components may be provided. For example, a network or network connection is provided, such as for networking with a medical imaging network or data archival system. In another example, the user input 85 is not provided. As another example, a server is provided for implementing the image processor 82 and/or machine-learnt classifiers 90 remotely from the medical scanner 80.

The image processor 82, memory 84, user input 85, display 86, and/or machine learnt classifiers 90 are part of the medical scanner 80. Alternatively, the image processor 82, memory 84, user input 85, display 86, and/or machine learnt classifiers 90 are part of an archival and/or image processing system, such as associated with a medical records database workstation or server, separate from the medical scanner 80. In other embodiments, the image processor 82, memory 84, user input 85, display 86, and/or machine learnt classifiers 90 are a personal computer, such as desktop or laptop, a workstation, a server, a network, or combinations thereof.

The medical scanner 80 is a medical diagnostic imaging scanner. Ultrasound, CT, x-ray, fluoroscopy, positron emission tomography, single photon emission computed tomography, and/or magnetic resonance systems may be used. The medical scanner 80 may include a transmitter and includes a detector for scanning or receiving data representative of the interior of the patient.

In one embodiment, the medical scanner 80 is a CT scanner. A gantry supports a source of x-rays and a detector on opposite sides of a patient examination space. The gantry moves the source and detector about the patient. Various x-ray projections are acquired by the detector from different positions relative to the patient. Computed tomography solves for the two or three-dimensional distribution of the response from the projections.

The memory 84 may be a graphics processing memory, a video random access memory, a random access memory, system memory, cache memory, hard drive, optical media, magnetic media, flash drive, buffer, database, combinations thereof, or other now known or later developed memory device for storing data or video information. The memory 84 is part of the medical scanner 80, part of a computer associated with the image processor 82, part of a database, part of another system, a picture archival memory, or a standalone device.

The memory 84 stores medical imaging data representing the patient, parsing, feature kernels, extracted values for features, classification results, machine-learnt matrices, and/or images. The memory 84 may alternatively or additionally store data during processing, such as storing information discussed herein.

The memory 84 or other memory is alternatively or additionally a non-transitory computer readable storage medium storing data representing instructions executable by the programmed image processor 82 or a processor implementing the machine-learnt classifiers 90. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The image processor 82 is a general processor, central processing unit, control processor, graphics processor, digital signal processor, three-dimensional rendering processor, application specific integrated circuit, field programmable gate array, digital circuit, analog circuit, combinations thereof, or other now known or later developed device for detecting different organs or regions from results of scanning. The image processor 82 is a single device or multiple devices operating in serial, parallel, or separately. The image processor 82 may be a main processor of a computer, such as a laptop or desktop computer, or may be a processor for handling some tasks in a larger system, such as in the medical scanner 80. The image processor 82 is configured by instructions, design, hardware, and/or software to perform the acts discussed herein.

The image processor 82 is configured to perform the acts discussed above. The image processor 82 is configured to detect multiple organs and/or regions from results of the scanning. Scan data is parsed, labeling different organs and/or regions. The detection occurs without user input of any location on an image. In alternative embodiments, input from the user is used as a seed or tracing to aid in detecting the multiple organs. Template matching, segmentation, thresholding, filtering, or other image processing is applied to the scan data to detect.

The image processor 82 may be configured to calculate values for features and input the values to a machine-learnt classifier to detect one or more organs or regions. The image processor 82 may be configured to generate a user interface or the GUI 88 for receiving seed points or designation of a region of interest on one or more images and/or for outputting results of the detection or the outputs of the machine-learnt classifiers 90.

The machine-learnt classifiers 90 are implemented by the image processor 82 or other processor with access to the matrices defining the classifiers 90 stored in the memory 84. The machine-learnt classifiers 90 are matrices of inputs (i.e., values of features in the input vector), weights, relationships between weighted inputs or other layers, and outputs of cause and/or probability of cause.

Any machine training may be used to create the machine-learnt classifiers 90. For example, a support vector machine is used. As another example, deep learning is used to both train the classifier and learn distinguishing features (e.g., convolution or filter kernels to extract determinative information from the scan data). The machine-learnt classifiers 90 are trained to relate input values to causes of abdominal pain. The probability of any given cause being a particular patient's source of abdominal pain may be estimated by one of the machine-learnt classifiers 90.

A plurality of machine-learnt classifiers 90, such as deep-learnt classifiers, are provided. At least one machine-learnt classifier 90 is provided for each of the detected organs or regions. For a given organ or region, one machine-learnt classifier 90 may detect different causes, separate machine-learnt classifiers 90 may detect the different causes, or a cascade or hierarchy of machine-learnt classifiers 90 may detect the different causes. The array of machine-learnt classifiers 90 provides focused, yet comprehensive, detection of sources of abdominal pain to assist the physician in localizing the cause of pain.

The GUI 88 includes one or both of the user input 85 and the display 86. The GUI 88 provides for user interaction with the image processor 82, medical scanner 80, and/or machine-learnt classifiers 90. The interaction is for inputting information (e.g., selecting patient files) and/or for reviewing output information (e.g., viewing an image showing different causes and respective predications of the probabilities of the causes being a source of a given patient's abdominal pain). The GUI 88 is configured (e.g., by loading an image into a display plane memory) to display the detected causes, including the respective probabilities.

The user input device 85 is a keyboard, mouse, trackball, touch pad, buttons, sliders, combinations thereof, or other input device. The user input 85 may be a touch screen of the display 86. User interaction is received by the user input device 85, such as a designation of a region of tissue (e.g., a click or click and drag to place a region of interest). Other user interaction may be received, such as for activating the classification.

The display 86 is a monitor, LCD, projector, plasma display, CRT, printer, or other now known or later developed devise for outputting visual information. The display 86 receives images, graphics, text, quantities, or other information from the image processor 82, memory 84, medical scanner 80, or machine-learnt classifiers 90.

One or more images are displayed. The images may or may not include anatomical representation or imaging. The image includes causes. Indications of probability of one or more causes being a source of the pain are included in the image. The image includes an indication, such as a text, a graphic or colorization, of the classification or detection of the source of pain. Alternatively or additionally, the image includes a quantity based on the detection or classification.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for identifying a source of abdominal pain, the method comprising:
   scanning a patient with a computed tomography scanner, the scanning providing data representing an abdomen of the patient;
   parsing, by an image processor, the data into a first portion representing a first organ and a second portion representing a second organ, the first and second organs being abdominal organs;
   applying one or more first deep-learnt machine-trained classifiers to the first portion of the data by input of the data of the first portion to the one or more first deep-learnt machine-trained classifiers, the application resulting in output by the one or more first deep-learnt machine-trained classifiers of first likelihoods of multiple causes of pain for the first organ, the first deep-learnt machine-trained classifiers comprising first neural networks;
   applying one or more second deep-learnt machine-trained classifiers to the second portion of the data, by input of the data of the second portion to the one or more second deep-learnt machine-trained classifiers the application resulting in output by the one or more second deep-learnt machine-trained classifiers of second likelihoods of multiple causes of pain for the second organ, the second deep-learnt machine-trained classifiers comprising second neural networks; and
   generating an image of the patient from the data, the image including a plurality of the first and second likelihoods and the respective causes.

2. The method of claim 1 wherein scanning, parsing, applying the one or more first deep-learnt machine-trained classifiers, applying the one or more second deep-learnt machine-trained classifiers, and generating are performed during an emergency room visit by the patient.

3. The method of claim 1 wherein parsing comprises parsing with a third machine-learnt classifier.

4. The method of claim 3 wherein parsing comprises parsing the first portion with the third machine-learnt classifier and parsing the second portion with a fourth machine-learnt classifier.

5. The method of claim 1 wherein applying the one or more first deep-learnt machine-trained classifiers comprises applying just one first deep-learnt machine-trained classifier with the resulting first likelihoods of the multiple causes output by the just one first deep-learnt machine-trained classifier.

6. The method of claim 1 wherein applying the one or more first deep-learnt machine-trained classifiers comprises applying separate ones of the first deep-learnt machine-trained classifiers for each of the multiple causes.

7. The method of claim 1 wherein applying the one or more first deep-learnt machine-trained classifiers comprises outputting by the one or more first deep-learnt machine-trained classifiers the first likelihoods where the multiple causes comprise tumor, inflammation, stone, and bleeding.

8. The method of claim 1 wherein generating comprises generating the image with the plurality of the first and second likelihoods comprising a threshold limited number of the first and second likelihoods.

9. The method of claim 1 wherein generating comprises generating with values of the first and second likelihoods assigned to incremental ranges of at least 10% for each increment.

10. The method of claim 1 further comprising:
    outputting clinical decision support with the image.

11. The method of claim 1 further comprising:
    identifying a previous case in a database based on the first and/or second likelihoods; and
    retrieving the previous case from the database.

* * * * *